Figure 8:
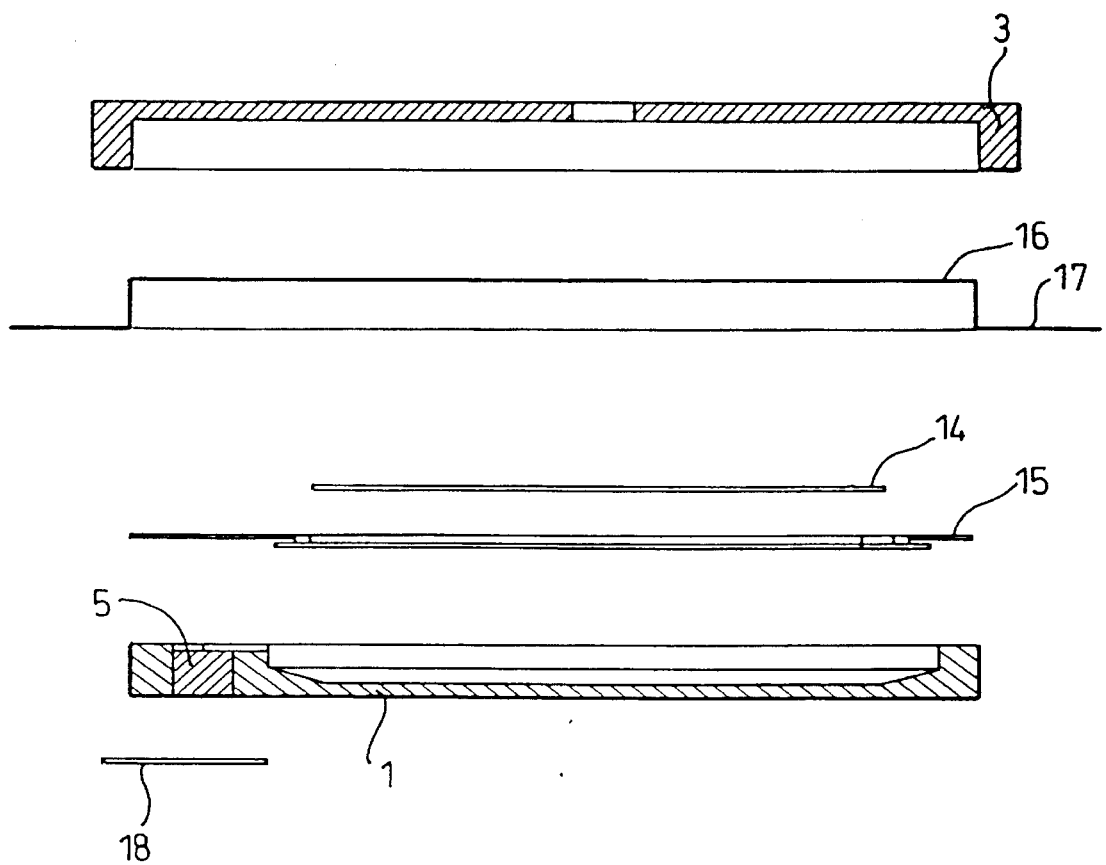

United States Patent [19]

Sarzaud et al.

[11] Patent Number: 5,558,664
[45] Date of Patent: Sep. 24, 1996

[54] DEVICE FOR THE DERMAL ABSORPTION OF MEDICINAL SOLUTES

[76] Inventors: F. X. Sarzaud, 4 Square Villaret de Joyeuse, F-75017 Paris; Jean Perego, 2, rue du Cheffin, F-21250 Seurre; A. Cabrera, 15, boulevard de Levallois, F-92200 Neuilly-sur-Seine, all of France

[21] Appl. No.: 177,736

[22] Filed: Jan. 4, 1994

[30] Foreign Application Priority Data

Jul. 5, 1991 [FR] France .................................... 91 08483

[51] Int. Cl.$^6$ ..................................................... A61K 9/22
[52] U.S. Cl. ........................ 604/890.1; 604/238; 424/449
[58] Field of Search ............................ 604/890.1, 892.1, 604/19, 236–238; 424/DIG. 7, 447–449

[56] References Cited

U.S. PATENT DOCUMENTS

| | | | |
|---|---|---|---|
| 4,619,652 | 10/1986 | Eckenhoff | 604/892.1 |
| 5,084,008 | 1/1992 | Phipps | 604/20 |
| 5,087,241 | 2/1992 | Mathiesen et al. | 604/20 |
| 5,088,978 | 2/1992 | Hillman | 604/20 |
| 5,122,127 | 6/1992 | Stanley | 604/890.1 |
| 5,257,987 | 4/1993 | Athayde | 604/892.1 |
| 5,358,483 | 10/1994 | Sibalis | 604/20 |

FOREIGN PATENT DOCUMENTS

| | | | |
|---|---|---|---|
| 0113562 | 7/1984 | European Pat. Off. . | |
| 0114125 | 7/1984 | European Pat. Off. . | |
| 2678514 | 1/1993 | France . | |
| 9103271 | 3/1991 | WIPO . | |
| 9303693 | 3/1993 | WIPO | 604/890.1 |
| 9409848 | 5/1994 | WIPO | 604/892.1 |

Primary Examiner—C. Fred Rosenbaum
Assistant Examiner—Chalin Smith
Attorney, Agent, or Firm—Nilles & Nilles, S.C.

[57] ABSTRACT

The device consists of: (a) an application reservoir or cell (1) whose base has a filling hole (4) for the solution and an opening that is fitted with a stopper (5) which presents micro-recesses on its periphery for administration of the solution on the skin; (b) a balloon (2) to pressurize and stabilize flow of the solution within the reservoir; and (c) a lid (3) to hermetically seal the aforesaid reservoir. The device is used in the form of a bracelet, abdominal belt or patch for application of solutions like trinitrine, oestradiols, etc. onto the skin.

21 Claims, 2 Drawing Sheets

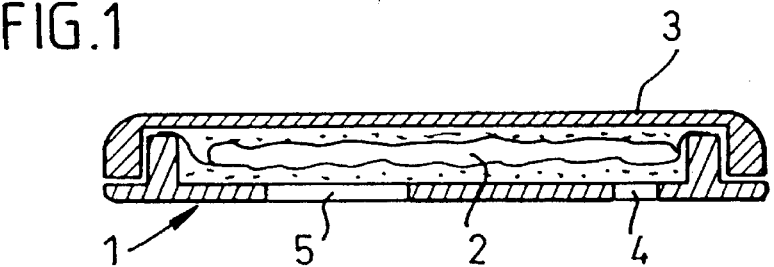
FIG.1
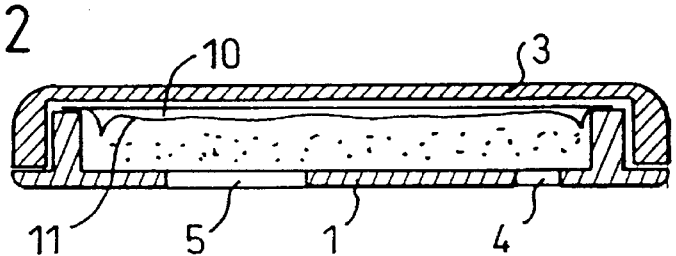
FIG.2
FIG.4
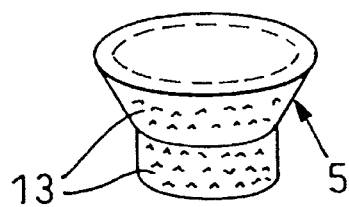
FIG.5
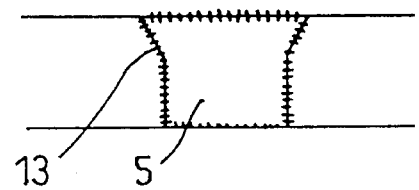
FIG 3
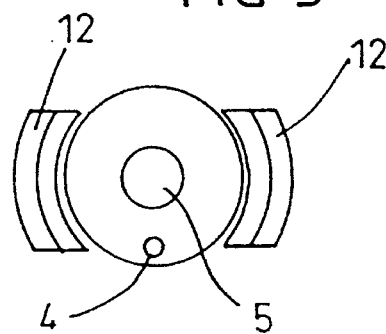
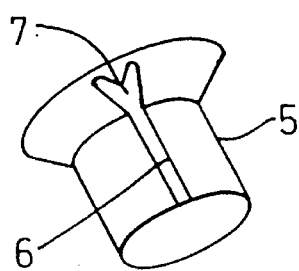
FIG.6
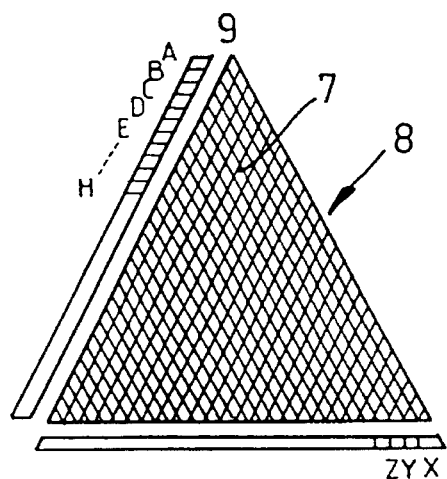
FIG.7

DEVICE FOR THE DERMAL ABSORPTION OF MEDICINAL SOLUTES

This case is a continuation of PCT/FR92/00617, filed Jul. 1, 1992 and published Jan. 21, 1993, which is in turn claims priority to French Application No. 91-08483, filed Jul. 5, 1991.

This invention relates to the field of transdermic drug application systems and covers a perfected device for cutaneous administration of drug solutions.

Systems and devices in the form of adhesive skin patches containing drug solutions with different active agents have been developed and marketed for several years. Such devices and systems can supply very low doses of the relevant drug, for example 1 microgram at 20 mg per day for 2 to 30 days or longer. Applications of such devices and systems include, amongst others, the administration of trinitrine for heart diseases, of estradiol for the treatment of menopause, etc.

The systems currently in use are of two types (those with membranes and those referred to as "matrix" systems) and use the migration principle subject to FICK's law (as well as STOCK and STEIN) according to which the speed of migration depends on the concentration gradient between the two compartments, with the molecules moving from the most concentrated to the least concentrated. The speed decreases when the viscosity of the medium increases or when permeability is low.

In the membrane system, the reservoir which contains the active agent solute is sealed by a membrane placed on the skin and permeable only to the active agent. This membrane is covered with an adhesive which makes it possible to fix the patch on the skin and to provide a solution of continuity with the latter.

In the matrix system, the reservoir is replaced with an absorbent substance, a sort of molecular sponge which can be the adhesive substance itself. The side touching the skin is also adhesive and provides continuity surface with the skin.

In such systems, the matrix, membrane and adhesive act as barriers substantially hindering migration of the active agent to the skin. Despite the regulation effect wanted, flow of the active agent which migrates into the skin always takes an inverse exponential form over time. Strong concentrations of the active agent are thus required in the system to obtain relatively strong local pressure. Migration should then be curbed to produce continuous strongly attenuated, inverse exponential flow. Another way of obtaining strong local pressure is described in European patent EP-A-0113562 in which the matrix is pressurized by a mobile plate forming a piston. A series of measurements of migration and absorption have shown that membrane and matrix patches, designed to supply set amounts of the active agent ranging from 20 to 25 mg at a rate of 5 mg per day, only give approximately 20 to 30% yields.

Furthermore, the adhesive which acts as a solution of continuity for migration of the active agent takes several hours to adapt to the skin surface and stick, thus delaying the therapeutic effect. Drug overdose, lasting for 1 or 2 hours, has often been observed after adherence of the adhesive due to migration over a very short distance of molecules close to the surface in contact with the skin. The adhesive forms an occlusion zone on the surface of the skin, i.e. the adhesive prevents sweat from evaporating. If the active agent is not soluble in water (e.g. trinitrine and oestradiol) this occlusion effect substantially perturbs or even prevents migration. Lastly, this same effect may loosen or detach the patch with dramatic consequences for the patient, e.g. in cases of myocardial infarction.

The invention is designed to overcome this series of problems and provides a new transdermic application system offering an array of advantages not yet attained elsewhere, including: efficacy, reliability at low cost, lack of adhesive on the part of the skin receiving the active agent, self flow regulation despite variations in skin permeability (over time and according to patients) and the possibility of regular depositing of the active agent over a period of 8 days, 15 days or longer.

To solve these problems, this new device, designed for the transcutaneous administration of drug solutions, has the following main features: a) an application reservoir or cell whose base has a filling hole for the solution and an opening that is fitted with a stopper which presents micro-recesses on its periphery for distribution of the solution on the skin, (b) a pressure means to pressurize and stabilize flow of the solution within the reservoir and (c) a lid to hermetically seal the aforesaid reservoir.

The micro-recesses in this invention can be produced by different methods.

According to a first embodiment the micro-recesses are made through roughness produced by moulding the stopper by electro-erosion. In practice, roughness indices of No. 33 to 21 can be used, corresponding to maximum distances or heights between the peaks or troughs in recesses of 4.5 to 1.2 microns. The stopper should be conically shaped overall or have a conical head whose initial diameter is the same as that of the body of the stopper.

According to another embodiment the micro-recesses are made by indenting the stopper with either a mini-notch made parallel to the stopper axis and forming a ring-shaped canal flared out triangularly at the end in contact with the skin. This system, which we shall return to later, enables the solution of active agent to cross the indentation and circulate along the perimeter of the circumference by capillarity. The solution then diffuses throughout the covered area.

According to the invention, the first way of producing pressure is by a plastic film balloon filled with a mixture of Freons.

This hollow balloon should be made (but not exclusively) of polyethylene film stuck onto polyamide film using an adhesive such a dual-ingredient polyurethane glue. A variant is to replace this balloon with a flat plastic film, either simple or complex above. In this case, there is a joint on the inner edge of the lid, sealing the film and exerting pressure on it when the device is closed.

As stated above, the balloon contains a mixture of freons in either a gaseous or liquid form according to the conditions of use (application of the patch or storage of the patch in the cold). For the variant discussed above, where the balloon is replaced by a film, the said mixture, which is liquid at ordinary temperatures, is deposited on the inner wall of the reservoir. In practice the following types of Freons can be used: Freon 11 and 113 in roughly equal proportions.

According to another characteristic of the invention, the drug solutions applied by the invented device can be mixed with a small amount of Freon and propanediol-1,2 mixture. This addition stabilizes the pressure system.

The pressure means can also be constituted, in an interesting second variant of the invention, of a spring which presses onto a plastic film.

This film can be folded onto itself, forming a gusset, or can form a balloon-shaped hollow volume. In both cases, it presses, through action of the spring, onto the top of the reservoir containing the solution.

Other characteristics will be given by the ensuing descriptions of examples of systems shown in the illustrations. They give a schematic representation of the following:

FIG. 1. General sectional view of the first variant of the device;

FIG. 2. Another variant of the inside of the device;

FIG. 3. View of the top of the device;

FIGS. 4 and 5. Perspective and sectional views of a stopper with rough walls with micro-recesses;

FIG. 6. Diagram showing a drainage indentation made at the edge of the stopper; and FIG. 7. Enlarged illustration of a flared indentation (taking the form of an equilateral triangle).

FIG. 8. Overall sectional view of the second variant of the device.

As can be seen in FIGS. 1 to 7, a device complying with the invention has the following basic features: an application reservoir 1 or cell in which a balloon or plastic film 2 and sealing lid 3 are added. The reservoir wall has a filling hole 4 (with sealing cap, not shown) and a conically shaped stopper 5.

A large number of studies conducted on this invention to produce a stopper with a very small cross-section active flow drainage hole (e.g. 0.3 to 5 microns) and high dimensional stability, have led to the selection of criteria and factors favouring the best results. These include: producing nylon, polypropylene or equivalent plastic stoppers by injection moulding; producing micro-recesses on the edges and outer surfaces of the stoppers to obtain a rough surface or reproducible indentation by electro-erosion moulding; selection of an indentation with a triangular base (preferably an equilateral triangle) from where the active fluid flows.

FIGS. 4 and 5 show an excellent stopper design 5 with a conical head and outer sides of which present roughenesses 13 made during electro-erosion moulding, and corresponding to roughness indices ranging for example from No 39 to 21.

FIG. 6 shows another type of stopper, also with a conical head, where active flow is no longer drained through micro-recesses due to surface roughness but through surface indentation 6 with a flared end 7.

FIG. 7 shows an indentation base in the shape of an equilateral triangle. This design gives extremely fine, rigourous setting, during production of the part by electro-erosion, and the fluid flow rates required. For example, rough setting is performed first by attacking one of the triangle's sides, e.g. side 8 (FIG. 6) by wearing mini-sections X, then Y and then Z. For finer setting, apex 9 is then attacked, for example in mini-sections A, B, C ... E.

The indentation (or flare) surface naturally has to be adjusted in function of variables such as: viscosity of the active solution, pressure exerted by the balloon (as explained hereafter) and skin temperature (which ranges from 34.7° to 35.2° C.).

Instead of an equilateral triangle, a triangle with a lower apex can be used, e.g. 20 degrees, or a half-moon shaped form.

According to a basic characteristic of the invention, a pressure means is used inside the reservoir 1 to slightly compress the drug solution on stopper 5 (this pressure can vary, for example, from $5.10^3$ to $5.10^4$ Pascals (Pa)) and to force it to drain through the roughness 13 or to flow into the indentation 6. As shown in FIG. 1, this pressure means consists of balloon 2 made of plastic film welded at its edges and cut into a circular shape. The plastic film should preferably be made of a polyethylene based complex stuck onto polyamide film with polyurethane adhesive. FIG. 2 shows a variant where the inner perimeter of the lid 3 has a joint 10, for example made of silicon, to seal the device and hold the plastic film 11, acting as the balloon. The lid thus acts in this instance as one of the balloon's walls.

The balloon is filled with a mixture of Freons, and in the case of the variant shown in FIG. 2., the mixture used is placed on the wall of the lid. This type of mixture, for example containing roughly equal proportions of Freon 11 and 113, produces very low pressure, in the order of $2.10^4$ Pa and does not produce any detectable leaks even after one year. This is also due to the drug solution containing propyleneglycol in addition to Freons. This produces a perfect vapour pressure and solute migration balance when the patch is at ordinary temperature.

FIG. 8 shows a particularly advantageous pressure and solution flow regulation means.

In this exploded view, the solution reservoir 1, fitted with a conical stopper 5 and a filling aperture (located behind the aforesaid stopper and not shown in the figure) is the support surface for a gusset 15, made of folded plastic film (or alternatively in the form of a balloon).

The solution is gradually released by continuous pressure of the spring 14 on the gusset 15.

Between the spring 14 and lid 3 of the device, there is a thin plastic film 16 whose ends 17 are coated in adhesive to stick the device onto the skin.

In practice, each component of the device according to the invention is similarly shaped (extra-flat) and can be made of moulded or compressed plastic by electro-erosion, as described above, to create impressions in the stopper and surface roughnesses or, depending on the variant, indentation. As shown in FIGS. 3 and 8, the apparatus is often supplied with adhesive pads 12 and 17 that stick to the skin. Other models of the device are also available in the form of bracelets, and belts for abdominal application (particularly for trinitrine solutions used as coronary dilators in myocardial infarction).

Other dimensions can of course be used for the invented device. For example, an experimental model was made using the first method, shown in FIGS. 1 to 7, with a diameter of approximately 40 mm, thickness 2.8 mm when closed, and stopper diameter of approximately 0.5 mm for 0.8 mm stopper thickness. The volume of the reservoir was approximately 1.2 ml. Using a roughness index of 27, corresponding to a maximum distance between peaks and troughs of 2.24 microns, the stopper fitted particularly tightly into the cell and the drug solution flow rate obtained was approximately 1.2 ml over a total period of 8 days.

A confirmed example or embodiment is illustrated in FIG. 8, which shows an oblong model, 41 mm by 46 mm, and 3.2 mm thick with a 1.4 ml reservoir.

The extra-flat spring 14 applied a force of approximately 0.9 kg on the gusset 15 and hence on the solution.

The solution escapes through the dosage and diffusion stopper 5 and flows out onto the surface in contact with the skin.

The commissioning aperture 18 is removed when the device is placed on the skin.

The systems in the invention are self-regulating.

Specifically, the higher skin permeability is to the active agent, the smaller the surface of skin required to absorb the solution.

Dosage of the solution is extremely precise as its mechanical release is extremely precise.

Apart from the above mentioned cases of application of the invention, use of this device can be recommended for the administration of nicotine or other substances during withdrawal programmes.

We claim:

1. A device for transcutaneous drug administration, comprising:
   (a) an application reservoir including a base, said base including a filling hole and an opening;
   (b) a means to pressurize said application reservoir, said means being connected to said application reservoir;
   (c) a lid connected to said application reservoir, said lid hermetically sealing said application reservoir; and
   (d) a stopper fitted in said opening of said base,
   wherein said stopper includes micro-recesses on a periphery of said stopper that collaborate with the opening to produce at least one drug drainage hole with a a cross-section that provides regular drug flow.

2. A device according to claim 1, wherein the means includes a balloon said balloon including a plastic film that is filled with a mixture of freons.

3. A device according to claim 2, wherein the balloon includes a polyethylene film laminated to a polyamide film with a dual ingredient polyurethane glue.

4. A device according to claim 2, wherein the mixture of freons in the balloon includes approximately the same amounts of Freon 11 and Freon 113.

5. A device according to claim 1, wherein the means to pressurize said application reservoir includes a spring which presses onto a plastic film.

6. A device according to claim 5, wherein the plastic film defines a shape selected from the group consisting of a gusset and a balloon, said plastic film pressing onto a top of the application reservoir.

7. A device according to claim 1, wherein an outer surface of the stopper defines a conical shape.

8. A device according to claim 1, wherein the micro-recesses of the stopper are surface roughnesses obtained by electro-erosion.

9. A device according to claim 1, wherein the micro-recesses of the stopper define an indentation at an edge of the stopper.

10. A device according to claim 9, wherein said indentation at the edge of the stopper is parallel to an axis of the stopper and forms a ring-shaped canal that is flared out triangularly at an end of the stopper.

11. A device according to claim 1, wherein the device, the application reservoir, the means and the lid are circular, flat and include injection moulded plastic, the micro-recesses of said stopper being made by electro-erosion of injection moulded plastic.

12. A device according to claim 1, further comprising one member selected from the group consisting of a bracelet, an abdominal belt and a lateral adhesive pad.

13. A device according to claim 1, wherein the micro-recesses are formed so as to permit the application by dermic absorption of drug solutions, said drug solutions including i) at least one active agent of the group consisting of trinitrine, oestradiols and nicotine and ii) a mixture including freon and propanediol-1,2.

14. A device according to claim 2, wherein the micro-recesses of the stopper are surface roughnesses obtained by electro-erosion.

15. A device according to claim 5, wherein the micro-recesses of the stopper are surface roughnesses obtained by electro-erosion.

16. A device according to claim 2, wherein the micro-recesses of the stopper define an indentation at an edge of the stopper.

17. A device according to claim 16, wherein said indentation at the edge of the stopper is parallel to an axis of the stopper and forms a ring-shaped canal that is flared out triangularly at an end of the stopper.

18. A device according to claim 5, wherein the micro-recesses of the stopper define an indentation at an edge of the stopper.

19. A device according to claim 18, wherein said indentation at the edge of the stopper is parallel to an axis of the stopper and forms a ring-shaped canal that is flared out triangularly at an end of the stopper.

20. A device according to claim 2, wherein the device, the application reservoir, the means and the lid are circular, flat and include injection moulded plastic, said micro-recesses of said stopper being made by electro-erosion of injection moulded plastic.

21. A device according to claim 5, wherein the device, the application reservoir, the means and the lid are circular, flat and include injection moulded plastic, said micro-recesses of said stopper being made by electro-erosion of injection moulded plastic.

* * * * *